United States Patent
Suriye et al.

(10) Patent No.: US 11,383,225 B2
(45) Date of Patent: Jul. 12, 2022

(54) HYDROCARBON CONVERSION CATALYST SYSTEM

(71) Applicant: SMH Co., Ltd, Bangkok (TH)

(72) Inventors: Kongkiat Suriye, Samut-Prakan (TH); Amnart Jantharasuk, Thammarat (TH); Wuttithep Jareewatchara, Bangkok (TH)

(73) Assignee: SMH Co., Ltd, Bangkok (TH)

( * ) Notice: Subject to any disclaimer, the term of this patent is extended or adjusted under 35 U.S.C. 154(b) by 114 days.

(21) Appl. No.: 16/468,859

(22) PCT Filed: Nov. 30, 2017

(86) PCT No.: PCT/EP2017/080946
§ 371 (c)(1),
(2) Date: Jun. 12, 2019

(87) PCT Pub. No.: WO2018/108544
PCT Pub. Date: Jun. 21, 2018

(65) Prior Publication Data
US 2020/0070128 A1   Mar. 5, 2020

(30) Foreign Application Priority Data

Dec. 13, 2016 (EP) .................................. 16203690
Dec. 13, 2016 (EP) .................................. 16203692
Dec. 13, 2016 (EP) .................................. 16203696

(51) Int. Cl.
| | |
|---|---|
| *B01J 23/652* | (2006.01) |
| *B01J 23/30* | (2006.01) |
| *B01J 23/62* | (2006.01) |
| *B01J 37/02* | (2006.01) |
| *B01J 37/08* | (2006.01) |
| *C07C 5/333* | (2006.01) |

(52) U.S. Cl.
CPC .......... *B01J 23/6527* (2013.01); *B01J 23/30* (2013.01); *B01J 23/62* (2013.01); *B01J 23/626* (2013.01); *B01J 37/0201* (2013.01); *B01J 37/0203* (2013.01); *B01J 37/0236* (2013.01); *B01J 37/08* (2013.01); *C07C 5/3337* (2013.01); *C07C 2523/08* (2013.01); *C07C 2523/14* (2013.01); *C07C 2523/28* (2013.01); *C07C 2523/42* (2013.01); *C07C 2523/62* (2013.01); *C07C 2523/652* (2013.01)

(58) Field of Classification Search
CPC ....... C07C 5/333; C07C 5/3337; C07C 5/321; B01J 23/6527; B01J 23/30; B01J 23/62; B01J 23/626; B01J 37/0201; B01J 37/0203; B01J 37/0236; B01J 37/08
See application file for complete search history.

(56) References Cited

U.S. PATENT DOCUMENTS 3,980,721 A * 9/1976 Juguin .................... B01J 23/64
585/430
2010/0274063 A1   10/2010 Wang et al.

FOREIGN PATENT DOCUMENTS

| EP | 2689843 A1 * | 1/2014 | ............ B01J 23/626 |
| EP | 2689843 A1 | 1/2014 | |
| EP | 3050621 A1 | 8/2016 | |
| EP | 3069788 A1 | 9/2016 | |
| WO | WO-2014163590 A1 * | 10/2014 | .............. B01J 21/10 |
| WO | WO-2016005896 A2 * | 1/2016 | .......... B01J 23/6484 |

OTHER PUBLICATIONS

Feb. 20, 2018, International Search Report and Written Opinion, PCT/EP2017/080946.

* cited by examiner

*Primary Examiner* — Youngsul Jeong
(74) *Attorney, Agent, or Firm* — Banner & Witcoff, Ltd.

(57) ABSTRACT

The present invention relates to a hydrocarbon conversion catalyst system comprising: a first composition comprising a dehydrogenation active metal on a solid support; and a second composition comprising a transition metal on an inorganic support and a hydrocarbon conversion process utilizing the hydrocarbon conversion catalyst system.

19 Claims, No Drawings

HYDROCARBON CONVERSION CATALYST SYSTEM

CROSS-REFERENCE TO RELATED APPLICATIONS

This application is a U.S. National Stage application under 35 U.S.C. § 371 of International Application PCT/EP2017/080946 (published as WO 2018/108544 A1), filed Nov. 30, 2017, which claims the benefit of priority to Application EP 16203696.6, filed Dec. 13, 2016; to Application EP 16203690.9, filed Dec. 13, 2016; and to Application EP 16203692.5 filed Dec. 13, 2016. Benefit of the filing date of each of these prior applications is hereby claimed. Each of these prior applications is hereby incorporated by reference in its entirety.

FIELD OF THE INVENTION

The present invention relates to a hydrocarbon conversion catalyst system which can be used in a process for conversion of a hydrocarbon feed comprising a saturated hydrocarbon compound to olefin products.

BACKGROUND OF THE INVENTION

Olefins, especially light olefins including ethylene and propylene, are valuable hydrocarbon products. They are useful for preparing a wide variety of end products, including ethylene oxide, propylene oxide, ethyl benzene, acetone, phenol, polyethylene, polypropylene, other polymers, and other petrochemical products. Even though the prices have fluctuated over time, the demands in the industry have still been continuously growing.

To serve industrial needs, many methods have been used to produce olefins. However, it is typically more economically attractive to produce olefins from lower valued feedstock such as paraffins. A conventional method for converting saturated paraffins to olefins is thermal cracking. This is a highly energy intensive method and product selectivity is difficult to be adjusted and controlled.

Catalytic cracking is a later developed method. With appropriate catalytic materials, generally zeolite-based materials, hydrocarbon cracking can occur at less severe operating conditions.

In the art, also processes are known converting saturated paraffins to olefins (with corresponding carbon numbers) by dehydrogenation utilizing an appropriate catalyst. The dehydrogenation may be followed by an appropriate metathesis step, in order to finally provide a modified olefin products distribution which fulfills highest industrial needs.

Diverse side reactions may take place during dehydrogenation and metathesis, for example the (re)hydrogenation of ethylene, propylene or butene which are otherwise preferred end products of a dehydrogenation reaction of ethane, propane or butane. Further, in the presence of hydrogen, hydrogenolysis and cracking of feed materials, such as propane, may occur. Thus, the development of hydrogen may be a drawback in further reacting obtained olefins.

Despite various methods disclosed for production of light olefins, such as ethylene and propylene, there still remains need for light olefins production process utilizing less value paraffin feed with improved economics and/or olefins yield relative to current technologies.

SUMMARY OF THE INVENTION

This invention relates to a hydrocarbon conversion catalyst system comprising:

a. a first composition comprising a dehydrogenation active metal on a solid support; and
b. a second composition comprising a transition metal on an inorganic support.

This invention also relates to a hydrocarbon conversion process utilizing the hydrocarbon conversion catalyst system.

DETAILED DESCRIPTION OF THE INVENTION

As described above, the present invention relates to a hydrocarbon conversion catalyst system comprising a first composition and a second composition. The first composition comprises a dehydrogenation active metal on a solid support. The dehydrogenation active metal refers to a group of metals that are efficient for dehydrogenation of a hydrocarbon. Dehydrogenation is a reaction in which hydrogen is detached from a molecule. In one embodiment, the dehydrogenation active metal is selected from the group consisting of platinum, palladium, iridium, chromium, and mixtures thereof. In one preferred embodiment, the dehydrogenation active metal is platinum. The dehydrogenation active metal may be present in various oxidation states, including their zero valence or elemental metal form and other oxidation states such as oxide form, or alternatively in more than a single oxidation states.

In one embodiment, the first composition contains 0.01 to 25 wt % of the dehydrogenation active metal, preferably 0.05 to 20 wt % of the dehydrogenation active metal, more preferably 0.1 to 5 wt % of the dehydrogenation active metal, based on the total weight of the first composition.

In one embodiment, the solid support is selected from aluminium oxide, silicon dioxide, zir-conium dioxide, titanium dioxide, magnesium oxide, calcium oxide, and mixtures thereof. In particular embodiments, the solid support is a mixed of at least two or more metal oxides at various weight ratios. For example, the solid support may be selected from the group consisting of a mixed of magnesium oxide and aluminum oxide, a mixed of calcium oxide and aluminum oxide, and mixture thereof, preferably a mixed magnesium oxide and aluminum oxide. The mixed metal oxide solid support may be present as, or derived from, a layered double hydroxide (LDH) such as magnesium-aluminum LDH or calcium-aluminum LDH. Representatively, the mixed metal oxide solid support can preferably obtained by subjecting a layered double hydroxide, such as magnesium-aluminum or calcium-aluminum layered double hydroxide, to a temperature in the range of 600-700° C., more preferably 600-650° C., for more than 2 hours, more preferably 3 to 10 hours.

Additional active metal, which acts to enhance catalytic activity of this first composition, such as potassium, tin, lanthanum, indium, yttrium, ytterbium, rhenium, and mixtures thereof, may be also present in the first composition. In one preferred embodiment, the first composition further comprises an additional active metal selected from the group consisting of tin, indium, and a mixture thereof.

Preferably, the first composition contains 0.005 to 2 wt % of the additional active metal, more preferably 0.01 to 1 wt %, based on the total weight of the first composition.

In a representative embodiment, platinum is the dehydrogenation active metal, a mixed magnesium-aluminum oxide is the solid support, and tin is the additional active metals in the first composition.

The dehydrogenation active metal, the solid support, and the additional active metal may be present in a combined amount of generally at least about 90% by weight, typically at least about 95% by weight, and often at least about 99% by weight, of the first composition.

The second composition in the hydrocarbon conversion catalyst system comprises a transition metal on an organic support. Representative olefin metathesis active transition metal may include any one or more of those metals in Group 6 and Group 7 of the Periodic Table. In one embodiment, the transition metal of the second composition is selected from molybdenum, tungsten, rhenium, and mixtures thereof. The transition metal may be present in various oxidation states, including their zero valence or elemental metal form and other oxidation states such as oxide form, or alternatively in more than a single oxidation states.

The transition metal is preferably tungsten, more preferably in the form of tungsten oxide.

In one embodiment, the inorganic support is selected from aluminium oxide, silicon dioxide, zirconium dioxide, titanium dioxide, zeolite, and mixtures thereof, preferably silicon dioxide or a mixture of silicon dioxide and zeolite.

Preferably, the zeolite is selected from ZSM-5, X-zeolite, Y-zeolite, beta-zeolite, MCM-22, ferrierite, and mixtures thereof, more preferably Y-zeolite.

Particularly preferred for the second composition is the transition metal is dispersed, uniformly or possibly non-uniformly, on the inorganic support.

In one representative embodiment, the second composition comprises tungsten oxide dispersed on an inorganic support comprising a mixture of silicon dioxide and zeolite.

In another embodiment, the second composition further comprises a mixed metal oxide, preferably physically mixed with the transition metal dispersed on the inorganic support. The mixed metal oxide of the second composition may be preferably selected from a mixed of magnesium oxide and aluminum oxide and a mixed of calcium oxide and aluminum oxide. The mixed metal oxide of the second composition may be present as, or derived from, a layered double hydroxide (LDH) such as magnesium-aluminum LDH or calcium-aluminum LDH.

In one embodiment, the second composition contains 1 to 15 wt % of the transition metal, even more preferably 5 to 10 wt % of the transition metal, based on the total weight of the second composition.

The transition metal, the inorganic support, and the optional mixed metal oxide may be present in a combined amount of generally at least about 90% by weight, typically at least about 95% by weight, and often at least about 99% by weight, of the second composition.

In the hydrocarbon conversion catalyst system according to this invention, it may be provided that the first composition is different from the second composition. Likewise, the solid support comprised in the first composition may be different from the inorganic support comprised in the second composition.

In another embodiment, it may be provided that the second composition does not comprise the dehydrogenation active metal, in particular the second composition does not comprise platinum, palladium, iridium, chromium or mixtures thereof.

The first composition is preferably prepared by supporting all element precursors of the dehydrogenation active metal and the optional additional active metal on the solid support followed by a suitable heat treatment.

Similarly, the second composition is preferably prepared by supporting on the inorganic support all element precursors of the transition metal followed by a suitable heat treatment.

Element precursors are starting compounds containing the desired elements which can be converted to the desired form of the elements in the final hydrocarbon conversion catalyst by the suitable heat treatment. For example, the element precursors may include oxides, halides, alkoxides, nitrates, carbonates, formats, oxylates, amines, or hydroxides of the elements.

More preferably, the first composition is prepared by impregnating, preferably simultaneously (co-impregnation), the element precursors of the dehydrogenation active metal and the optional additional active metal, which are provided in solution form, on the solid support followed by calcination. The calcination is preferably carried out in oxidizing atmosphere, at a temperature in the range of 300-800° C. for 1-24 hours, even more preferably 400-600° C. for 2-10 hours.

In the embodiment where the second composition further comprises a mixed metal oxides as described above, the calcined transition metal on inorganic support is then further physically mixed with the selected mixed metal oxides, wherein the obtained mixture is then further calcine to obtain the final second composition.

Also more preferably, the second composition is prepared by impregnating, preferably sequentially, the element precursors of the transition metal, which are provided in solution form, on the inorganic support followed by calcination. The calcination is preferably carried out in oxidizing atmosphere, at a temperature in the range of 300-800° C. for 1-24 hours, even more preferably 400-600° C. for 2-10 hours.

The obtained first and second compositions from the preparation method described above are generally in the powder form with average size lower than 800 micrometers.

In one embodiment, the first composition and the second composition are physically mixed, preferably in a weight ratio of the first to the second composition from 1:10 to 10:1, more preferably 1:5 to 5:1, even more preferably 1:3 to 3:1, and even further preferably 1:2 to 2:1, to form the hydrocarbon conversion catalyst system.

The hydrocarbon conversion catalyst system can be in a powder form in one embodiment. In another embodiment, the hydrocarbon conversion catalyst system can be also formed into a shape that is more suitable for industrial utilization, for example, pellet, tablet, extrudate, or sphere.

Physical mixing of the first and the second compositions can be carried out before or after shaping of the hydrocarbon conversion catalyst system.

In one embodiment, the first composition and the second composition are separately formed into desired shapes, then the first composition formed into the desired shape and the second composition formed into the desired shape are physically mixed to obtain the hydrocarbon conversion catalyst system.

In another embodiment, powder of the first composition and powder of the second composition are physically mixed to obtain the hydrocarbon conversion catalyst system, and the obtained hydrocarbon conversion catalyst system may then be formed into any desired shape.

In shaping of the first composition, the second composition, or the hydrocarbon conversion catalyst system, a binding material can be added to facilitate formation of powder into the desired shapes. Any binding material known in the art may be used.

In another embodiment, it is also possible that the first and the second compositions are provided in macroscopic scale layer form, wherein the first composition and the second composition are arranged as separate layers in a fixed-bed reactor.

The inventive catalyst system is suitable to be used in a hydrocarbon conversion process. Preferably, the hydrocarbon conversion process comprises contacting a hydrocarbon feed stream with the hydrocarbon conversion catalyst system.

In order to achieve olefin products, it is favorable that the hydrocarbon feed stream comprises a paraffinic hydrocarbon. In an embodiment, the hydrocarbon feed stream comprises a paraffin having 2 to 5 atoms. In another embodiment, the hydrocarbon feed stream comprises a paraffin selected from ethane, propane, butane, pentane and mixtures thereof, preferably propane, butane, and a mixture thereof, even more preferably, the hydrocarbon feed stream is propane.

In case of a continuous flow system, the hydrocarbon feed stream as described above, can refer to a single feed stream or a total combined feed stream that includes, for example, other sources of paraffinic hydrocarbon(s) such as a recycle stream that comprises an unconverted portion of the paraffinic hydrocarbon feed stream that has been separated from the product. The hydrocarbon feed stream may, but does not necessarily, comprise only paraffinic hydrocarbons. For example, the feed generally comprises predominantly paraffinic hydrocarbons, typically comprises at least about 80% by weight of the hydrocarbon feed stream, and more often comprises at least about 90% by weight of the hydrocarbon feed stream.

The hydrocarbon conversion process can be operated in a wide range of operating conditions. However, some specific ranges of operating conditions can result in high olefins productions selectivity. In an embodiment, the process is carried out at a temperature in the range of 200-800° C., preferably 350-700° C., even more preferably 450-650° C. In another embodiment, the process is carried out at a pressure in the range of 0.01 to 10 bar gauge, preferably 0.05 to 5 bar gauge. The contact time needed to obtain a desirable yield of olefins products depends upon several factors, such as operating temperature, operating pressure, and catalyst activity. In one embodiment, the process is carried out at a weight hourly space velocity (WHSV) in the range of 0.01 to 20 $hr^{-1}$, preferably 0.05 to 5 $hr^{-1}$. The process can be conducted in a batch manner or continuous manner. For commercial scale, it is favorable that the process is continuously operated. Continuous operation can be performed with fixed bed, fluidized bed, or other techniques known in the art with fixed bed being typically preferred.

Prior to contacting with the hydrocarbon feed stream, the hydrocarbon conversion catalyst system may be optionally pretreated. The pretreatment condition may include contacting the catalyst system with an inert gas, an oxidizing gas, a reducing gas, and mixtures thereof at an elevate temperature, preferably 250° C. to 850° C., more preferably 400° C. to 750° C., even more preferably 500° C. to 700° C. In one preferred embodiment, the pretreatment condition includes contacting the catalyst with a reducing agent, more preferably hydrogen, at a temperature in the range of 400-600° C. for approximately 0.5 to 8 hours.

After contacted with the hydrocarbon feed stream at the operating conditions, some poisonous substances, heavy hydrocarbons, and coke may deposit on the surface of the hydrocarbon conversion catalyst system. This normally affects activity of the catalyst to gradually drop over time. A suitable regeneration can be performed on the used hydrocarbon conversion catalyst system to recover at least some of its activity. In an embodiment, the hydrocarbon conversion process comprises a regeneration step wherein regeneration step includes contacting the hydrocarbon conversion catalyst system with an oxidizing agent at a high temperature. The regeneration step should be carefully controlled to avoid overheating and destroying structure of the catalyst. In an embodiment, the regeneration step is carried out by contacting the used hydrocarbon conversion catalyst system with an oxidizing agent, preferably oxygen or air, at a temperature in the range of 200-700° C., preferably 300-600° C. Other known regeneration techniques can be employed without limitation.

The hydrocarbon conversion process generally further comprises obtaining a product stream comprising at least one, typically at least two, olefinic hydrocarbons. In an embodiment, the product stream comprises two olefinic hydrocarbons having different carbon numbers in relative to the paraffinic hydrocarbon comprised in the hydrocarbon feed stream. In a particular embodiment, the product stream comprises ethylene.

In a representative embodiment of the inventive hydrocarbon conversion process, the hydrocarbon feed stream comprises propane and the product stream comprises ethylene and butene.

It was surprisingly found that the inventive hydrocarbon conversion catalyst system, when used in a hydrocarbon conversion process, is capable of converting a paraffinic hydrocarbon, preferably propane, to at least one, typically at least two, olefinic hydrocarbons having different carbon numbers, preferably ethylene and butene, with higher selectivity in relative to existing (non-inventive) catalysts. In a representative embodiment, the hydrocarbon conversion process provide a total olefins selectivity of at least 20 wt %, preferably at least 40 wt %, and more preferably at least 60 wt %, wherein the total olefins selectivity is determined from total olefin products produced per pass divided by paraffinic hydrocarbon converted per pass expressed as a percentage.

Experimental Results

In the examples section below, the conversion of propane into olefins, preferably ethylene, propylene, and butene, has been investigated using various example embodiments of the hydrocarbon conversion catalysts system according to the present invention.

The features disclosed in the foregoing description and the claims may, both separately and in any combination thereof, be material for realizing the invention in diverse forms thereof.

Preparation of Catalyst

D1: 20 wt % platinum stock solution was prepared by dissolving 4.98 g chloroplatinic acid hydrate in 19.94 g ethanol. 0.2 g of 20 wt % platinum stock solution was dissolved again in 5 g ethanol, then loaded onto 5 g alumina support by incipient wetness impregnation method. The resulting sample was dried overnight at 110° C., then calcine under air at 620° C. for 2 hours.

D2: 20 wt % platinum stock solution was prepared by dissolving 4.98 g chloroplatinic acid hydrate in 19.94 g ethanol. 0.06 g of tin (ii) chloride dehydrate was dissolved in 5 g ethanol. Then 0.2 g of 20 wt % platinum stock solution was dissolved the resulting tin-ethanol solution. The resulting platinum-tin-ethanol solution was then loaded onto 5 g alumina support by incipient wetness impregnation method. The resulting sample was dried overnight at 110° C., then calcine under air at 620° C. for 2 hours.

D3: 20 wt % platinum stock solution was prepared by dissolving 4.98 g chloroplatinic acid hydrate in 19.94 g ethanol. 0.06 g of tin (ii) chloride dehydrate was dissolved in 5 g ethanol. Then 0.2 g of 20 wt % platinum stock solution was dissolved the resulting tin-ethanol solution. Magnesium aluminate (MgAlO3) mixed oxide was prepared by calcining LDH at 620° C. for 8 hours. The resulting platinum-tin-ethanol solution was then loaded onto 5 g magnesium aluminate support by incipient wetness impregnation method. The resulting sample was dried overnight at 110° C., then calcine under air at 620° C. for 2 hours.

D4: 20 wt % platinum stock solution was prepared by dissolving 4.98 g chloroplatinic acid hydrate in 19.94 g ethanol. 0.08 g of indium (iii) nitrate dehydrate was dissolved in 5 g ethanol. Then 0.2 g of 20 wt % platinum stock solution was dissolved the resulting indium-ethanol solution. The resulting platinum-indium-ethanol solution was then loaded onto 5 g alumina support by incipient wetness impregnation method. The resulting sample was dried overnight at 110° C., then calcine under air at 620° C. for 2 hours.

D5: 20 wt % platinum stock solution was prepared by dissolving 4.98 g chloroplatinic acid hydrate in 19.94 g ethanol. 0.08 g of indium (iii) nitrate dehydrate was dissolved in 5 g ethanol. Then 0.2 g of 20 wt % platinum stock solution was dissolved the resulting indium-ethanol solution. Magnesium aluminate (MgAlO3) mixed oxide was prepared by calcining LDH at 620° C. for 8 hours. The resulting platinum-indium-ethanol solution was then loaded onto 5 g magnesium aluminate support by incipient wetness impregnation method. The resulting sample was dried overnight at 110° C., then calcine under air at 620° C. for 2 hours.

M1: 1.072 g of ammonium metatungstate hydrate was dissolved in 13 g water. The resulting solution was loaded onto 10 g silica gel. The resulting sample was then dried overnight at 110° C., then calcine at 550° C. for 8 hours.

M2: 1.072 g of ammonium metatungstate hydrate was dissolved in 13 g water. The resulting solution was loaded onto a physical mixture of 9.5 g silica gel and 5 g HY zeolite. The resulting sample was then dried overnight at 110° C., then calcine at 550° C. for 8 hours. The calcined sample was then physically mixed with 1 g of magnesium aluminum layered double hydroxide.

Catalyst System Setup and Testing Condition

Test #1: The catalyst system was set up by loaded 1.5 g of D1 catalyst into a ¾" stainless steel reactor. Then the catalyst system was pretreated by introducing 100 sccm of air and 100 sccm of nitrogen into the reactor at 580° C. for 30 minutes, then 200 sccm of nitrogen was introduced to the reactor at 580° C. for 60 minutes, then 200 sccm of nitrogen and 50 sccm of hydrogen were consequently introduced into the reactor at 580° C. for 30 minutes. The catalyst system was then cooled down to 570° C. before introducing 30 sccm of 99.6 vol % propane reactant into the reactor under 1 atm pressure to start the reaction.

Test #2: The catalyst system was set up by physically mixed 1.5 g of D1 with 4 g of M1 and then loaded the mixture into a ¾" stainless steel reactor. Pretreatment of the catalyst system and paraffinic feed stream as same as Test #1 was used.

Test #3: The catalyst system was set up by loaded 1.5 g of D2 catalyst into a ¾" stainless steel reactor. Pretreatment of the catalyst system and paraffinic feed stream as same as Test #1 was used.

Test #4: The catalyst system was set up by physically mixed 1.5 g of D2 with 4.3 g of M2 and then loaded the mixture into a ¾" stainless steel reactor. Pretreatment of the catalyst system and paraffinic feed stream as same as Test #1 was used.

Test #5: The catalyst system was set up by loaded 1.5 g of D3 catalyst into a ¾" stainless steel reactor. Pretreatment of the catalyst system and paraffinic feed stream as same as Test #1 was used.

Test #6: The catalyst system was set up by physically mixed 1.5 g of D5 with 4.3 g of M2 and then loaded the mixture into a ¾" stainless steel reactor. Pretreatment of the catalyst system and paraffinic feed stream as same as Test #1 was used.

Test #7: The catalyst system was set up by physically mixed 1.5 g of D3 with 4.3 g of M2 and then loaded the mixture into a ¾" stainless steel reactor. Pretreatment of the catalyst system and paraffinic feed stream as same as Test #1 was used.

Test #8: 4.3 g of M2 was loaded into a ¾" stainless steel reactor followed by 1.5 g of D5. An amount of quartz wool was placed between M2 and D5 to separate the two layers. The reactor was positioned so that the D5 catalyst was on the top portion of the bed and the M2 catalyst was on the bottom portion of the bed of the catalyst system. Pretreatment of the catalyst system and paraffinic feed stream as same as Test #1 was used wherein all pretreatment gases and feed stream flew downward from top to bottom of the catalyst bed.

Test #9: 4.3 g of M2 was loaded into a ¾" stainless steel reactor followed by 1.5 g of D3. An amount of quartz wool was placed between M2 and D3 to separate the two layers. The reactor was positioned so that the D3 catalyst was on the top portion of the bed and the M2 catalyst was on the bottom portion of the bed of the catalyst system. Pretreatment of the catalyst system and paraffinic feed stream as same as Test #1 was used wherein all pretreatment gases and feed stream flew downward from top to bottom of the catalyst bed.

Test results are shown in Table 1.

It can be seen from the test results t catalyst systems that made of combination of the first composition (D) and the second composition) according to the present invention, increase of ethylene and butene selectivity are noticeably increased.

TABLE 1

| Test | C3H8 Conversion (wt %) | Selectivity (wt %) | | | | | |
|---|---|---|---|---|---|---|---|
| | | Total olefins | C3H6 | C2H4 | C4H8 | CH4 | C5+ |
| Reaction time on stream 3 hours | | | | | | | |
| #1 | 12.25 | 52.69 | 52.00 | 0.10 | 0.59 | 5.25 | 2.97 |
| #2 | 14.01 | 72.77 | 61.14 | 1.25 | 10.38 | 7.41 | 1.53 |
| #3 | 24.66 | 91.60 | 89.59 | 0.23 | 0.20 | 3.09 | 1.56 |
| #4 | 16.91 | 87.58 | 79.44 | 0.99 | 7.15 | 2.37 | 0.09 |
| #5 | 29.08 | 96.18 | 94.30 | 0.79 | 0.17 | 1.54 | 0.93 |
| #6 | 25.65 | 81.91 | 52.07 | 7.25 | 14.86 | 3.70 | 7.66 |
| #7 | 31.23 | 85.41 | 37.91 | 17.85 | 19.06 | 3.89 | 10.20 |
| #8 | 22.25 | 85.90 | 47.70 | 19.70 | 21.50 | 2.31 | 4.30 |
| #9 | 35.85 | 91.37 | 44.60 | 17.31 | 20.76 | 2.73 | 8.64 |
| Reaction time on stream 8 hours | | | | | | | |
| #1 | 11.20 | 56.08 | 41.59 | 3.65 | 10.84 | 5.30 | 2.96 |
| #2 | 10.92 | 82.08 | 70.54 | 1.88 | 9.66 | 5.96 | 1.06 |
| #3 | 25.79 | 93.64 | 91.97 | 0.40 | 0.16 | 2.44 | 1.09 |
| #4 | 14.32 | 92.91 | 85.32 | 1.26 | 6.33 | 1.36 | 0.04 |
| #5 | 28.08 | 96.48 | 94.60 | 0.86 | 0.17 | 1.48 | 0.85 |
| #6 | 20.31 | 75.22 | 48.07 | 6.76 | 13.52 | 5.57 | 6.74 |
| #7 | 30.11 | 85.10 | 38.06 | 17.83 | 18.87 | 4.01 | 10.12 |
| #8 | 15.31 | 84.80 | 45.80 | 21.40 | 20.20 | 3.00 | 4.90 |
| #9 | 35.77 | 90.12 | 41.87 | 18.54 | 20.50 | 2.95 | 9.08 |

The invention claimed is:

1. A hydrocarbon conversion catalyst system for dehydrogenation and metathesis of a hydrocarbon feed stream, said catalyst system comprising:
   a. a first composition comprising a dehydrogenation active metal on a solid support, said solid support comprising a mixed magnesium-aluminum oxide or a mixed calcium-aluminum oxide; and b. a second composition comprising a transition metal on an inorganic support said inorganic support comprising silicon dioxide or a mixture of silicon dioxide and zeolite, wherein the first composition is different from the second composition, and further wherein the first composition and the second composition are present in a weight ratio of 1:5 to 5:1, wherein the transition metal is selected from the group consisting of molybdenum, tungsten, rhenium, and mixtures thereof and is present in an amount from 1% to 15% by weight of the second composition, and wherein the first composition and the second composition are either physically mixed or configured as separate layers.

2. The hydrocarbon conversion catalyst system according to claim 1, wherein the dehydrogenation active metal is selected from the group consisting of platinum, palladium, iridium, chromium, and mixtures thereof.

3. The hydrocarbon conversion catalyst system according to claim 2, wherein the dehydrogenation active metal is platinum.

4. The hydrocarbon conversion catalyst system according to claim 1, wherein the mixed magnesium-aluminum oxide or the mixed calcium-aluminum oxide is derived from a layered double hydroxide.

5. The hydrocarbon conversion catalyst system according to claim 1, wherein the first composition further comprises an additional active metal selected from the group consisting of potassium, tin, lanthanum, indium, yttrium, ytterbium, rhenium, and mixtures thereof.

6. The hydrocarbon conversion catalyst system according to claim 5, wherein the additional active metal is selected from the group consisting of tin, indium, and mixture thereof.

7. The hydrocarbon conversion catalyst system according to claim 1, wherein the transition metal is selected from the group consisting of molybdenum, tungsten, rhenium, and mixtures thereof.

8. The hydrocarbon conversion catalyst system according to claim 7, wherein the transition metal is tungsten.

9. The hydrocarbon conversion catalyst system according to claim 1, wherein the zeolite is selected from the group consisting of ZSM-5, X-zeolite, Y-zeolite, beta-zeolite, MCM-22, ferrierite, and mixtures thereof.

10. The hydrocarbon conversion catalyst system of claim 1, wherein the dehydrogenation active metal is present in an amount from 0.01% to 25% by weight of the first composition.

11. The hydrocarbon conversion catalyst system of claim 2, wherein the dehydrogenation active metal is present in an amount from 0.01% to 25% by weight of the first composition.

12. The hydrocarbon conversion catalyst system of claim 1, wherein the first composition and the second composition are physically mixed.

13. The hydrocarbon conversion catalyst system of claim 2, wherein the first composition and the second composition are physically mixed.

14. A hydrocarbon conversion catalyst system for dehydrogenation and metathesis of a hydrocarbon feed stream, said catalyst system comprising:

a. a first composition comprising a dehydrogenation active metal on a solid support, said solid support comprising aluminum oxide, silicon dioxide, zirconium dioxide, titanium dioxide, magnesium oxide, calcium oside, or a mixture of two or more thereof; and b. a second composition comprising a transition metal on an inorganic support, said inorganic support comprising silicon dioxide or a mixture of silicon dioxide and zeolite, wherein the first composition is a different from the second composition, and further wherein the first composition and the second composition are present in a weight ratio of 1:5 to 5:1, wherein the transition metal is selected from the group consisting of molybdenum, tungsten, rhenium, and mixtures thereof and is present in an amount from 1% to 15% by weight of the second composition, wherein the first composition and the second composition are either physically mixed or configured as separate layers, and wherein the inorganic support further comprises a mixed metal oxide selected from (1) a mixture of magnesium oxide and aluminum oxide and (2) a mixture of calcium oxide and aluminum oxide.

15. A hydrocarbon conversion process comprising contacting a hydrocarbon feed stream with the hydrocarbon conversion catalyst system according to claim 1.

16. The hydrocarbon conversion process according to claim 15, wherein the hydrocarbon feed stream comprises a paraffin selected from the group consisting of ethane, propane, butane, pentane, and mixtures thereof.

17. The hydrocarbon conversion process according to claim 16, wherein the hydrocarbon feed stream is propane.

18. The hydrocarbon conversion process according to claim 15, wherein the hydrocarbon conversion process is carried out at a temperature in a range of 200 to 800° C.

19. The hydrocarbon conversion process according to claim 15, wherein the process further comprises obtaining a product stream comprising at least two olefinic hydrocarbons.

* * * * *